United States Patent
Oostveen

(10) Patent No.: US 9,783,347 B2
(45) Date of Patent: Oct. 10, 2017

(54) VALVE ASSEMBLY

(71) Applicant: Scholle Corporation, Northlake, IL (US)

(72) Inventor: Elmar Oostveen, Amsterdam (NL)

(73) Assignee: Scholle IPN Corporation, Northlake, IL (US)

( * ) Notice: Subject to any disclaimer, the term of this patent is extended or adjusted under 35 U.S.C. 154(b) by 161 days.

(21) Appl. No.: 14/788,655

(22) Filed: Jun. 30, 2015

(65) Prior Publication Data

US 2017/0001771 A1    Jan. 5, 2017

(51) Int. Cl.
*B65D 47/20* (2006.01)
*B65D 33/16* (2006.01)
*A61L 2/00* (2006.01)

(52) U.S. Cl.
CPC ............... *B65D 47/20* (2013.01); *A61L 2/00* (2013.01); *B65D 33/16* (2013.01)

(58) Field of Classification Search
CPC ....... B65D 47/20; B65D 33/16; F16K 39/028; F16K 1/222; F16K 1/2285; F16K 1/24; F16K 1/36; F16K 31/602; Y10T 137/9029
USPC ..... 251/305–308, 173, 175, 192, 90, 95, 98, 251/111, 900, 317.01; 137/800, 798
See application file for complete search history.

(56) References Cited

U.S. PATENT DOCUMENTS

| | | | | |
|---|---|---|---|---|
| 2,314,683 A | * | 3/1943 | Berry | F16J 15/32 251/900 |
| 3,593,960 A | * | 7/1971 | Scaramucci | F16K 1/2263 251/151 |
| 3,767,163 A | * | 10/1973 | Mueller | B67D 3/047 137/613 |
| 4,576,360 A | * | 3/1986 | Lew | F16K 1/224 251/162 |
| 5,307,955 A | | 5/1994 | Viegas | |
| 9,377,111 B2 | | 6/2016 | De Muinck et al. | |
| 2010/0044373 A1 | | 2/2010 | De Muinck et al. | |
| 2010/0276620 A1 | * | 11/2010 | Ezekiel | F16K 5/204 251/172 |

FOREIGN PATENT DOCUMENTS

RU             22980 U1 *   5/2002

* cited by examiner

*Primary Examiner* — Michael R Reid
(74) *Attorney, Agent, or Firm* — The Watson I.P. Group, PLC; Jovan N. Jovanovic; Vladan M. Vasiljevic

(57) ABSTRACT

A valve assembly comprising a valve housing, and a valve body. The valve housing having a lower end and an upper end. A valve seat is positioned therebetween. The valve seat being inclined inwardly toward the lower end. The valve body is pivotably positionable within the valve housing, and pivoting between a first closed orientation and a second open orientation. The valve body is pivotable about an axis that extends through the valve housing positioned between the upper end and the valve seat. In the first closed orientation, the valve body is configured to translate toward and away from the lower end of the valve housing.

14 Claims, 12 Drawing Sheets

VALVE ASSEMBLY

CROSS-REFERENCE TO RELATED APPLICATION

N/A

BACKGROUND OF THE DISCLOSURE

1. Field of the Disclosure

The disclosure relates in general to a valve assembly, and more particularly, to a valve assembly that is configured for steam sterilization in aseptic conditions (in the dispensing of foodstuffs such as liquids, purees, syrups, suspensions and the like). It will be understood that the valve is not limited to such use, and that use in other environments along with dispensing other flowable material is likewise contemplated.

2. Background Art

The use of valves to dispense flowable material from flexible packaging is known in the art. With the desire for higher flow rates, and the ability to discharge products having large particulates and solids, certain valves have been provided which fulfill such requirements.

At the same time as the performance demands have increased, the need for improved sanitization of the dispensing valves has necessitated more robust construction. For example, steam at elevated pressure is one of the predominant means by which to sterilize such valves. Problematically, such sterilization techniques have exposed the valves to harsh environments and harsh procedures.

Due to the elevated pressures and temperatures, many of the available valves have high failure rates. That is, the pressure and/or temperature damages components of the valves such that they are incapable of performing as required. Other designs are hampered by multiple components and redundancy to provide adequate strength to withstand such temperature and pressure. Still other solutions require the use of metal components and other heavy duty structures, thereby increasing the complexity and the cost of such valves.

SUMMARY OF THE DISCLOSURE

The disclosure is directed to a valve assembly comprising a valve housing and a valve body. The valve housing has a lower end and an upper end. The valve housing defining an inner bore. The valve housing including a valve seat spaced apart from the lower end and the upper end, separating the valve housing into a first valve side and a second valve side. The valve seat defining a seat surface that is inclined inwardly and toward the lower end of the valve housing.

The valve body includes an outer rim with an outer surface and a central web spanning therebetween. The outer rim includes at least two spaced apart outwardly directed annular flanges defining at least one channel therebetween, and a seal positioned within the at least one channel. The outer rim is inclined outwardly so as to correspond to the seat surface, with the valve body further having an axis of rotation extending transversely through the valve body spaced apart from the annular flanges.

The valve body is positioned within the inner bore of the valve housing, and pivotably coupled to the valve body along an axis of rotation that is positioned between the valve seat and the upper end of the valve housing. The valve body is positioned in a first closed orientation wherein the outer rim corresponds to the seat surface with the seal sealing the first valve side from the second valve side, and a second open orientation wherein the outer rim is pivoted away from the seat surface providing fluid communication between the first valve side and the second valve side. In the first closed orientation, the valve body is structurally configured to be translatable toward the lower end, thereby directing the outer rim toward the seat surface.

In some configurations, the valve body is structurally configured to be translatable toward the lower end, so as to direct the outer rim toward the seat surface, compressing the seal sufficiently to have a portion of the outer rim engage the seat surface.

In some configurations, the seal provides a biasing means sufficient to translate the valve body in the first closed orientation toward the upper end.

In some configurations, the valve body is translatable until each of the annular flanges engage the seat surface.

In some configurations, the at least two spaced apart outwardly directed annular flanges further comprise three spaced apart outwardly directed annular flanges, defining a first channel and a second channel therebetween. A seal is positioned within each of the first channel and the second channel.

In some configurations, the first channel has a first slope and the second channel has a second slope. The first slope and the second slope are different.

In some configurations, the three spaced apart outwardly directed annular flanges are substantially parallel to each other.

In some configurations, the valve assembly further includes a handle having a lever arm on the outside of the valve housing and a shaft extending through the housing. The shaft defines an axle member at a second end thereof. The valve housing has a valve axle slot opposite the axle member. The valve body further includes a first axle protrusion and a second axle slot. The first axle protrusion extends from the valve body and into the valve axle slot. The first axle protrusion is rotatable within the valve axle slot and translatable when the valve body is in the first closed orientation toward and away from the lower end. The second axle slot, with the axle member of the handle member extending into the second axle slot. The second axle slot is configured to impart rotation of the valve body upon rotation of the handle, and to allow translation of the valve body toward and away from the lower end when in the first closed orientation relative to the axle member.

In some configurations, the axle member and the valve axle slot define the axis of rotation of the valve body relative to the valve housing.

In some configurations, the axle member and the valve axle slot are positioned on the second side of the valve.

In some configurations, the valve assembly further includes a cap. The cap has an outer rim and a central body. The outer rim extending over the upper end of the housing, and sealingly engaging the valve housing at the upper end. The central body extends into contact with the valve body, with the central body precluding rotation of the valve body within the valve housing.

In some configurations, the central body includes a base and a base skirt extending from the base. The base and the base skirt being in contact with the central body in the first closed orientation, and precluding rotation of the valve body relative to the valve housing.

In some configurations, the valve housing further includes a base channel at the lower end. The base channel has an inner surface and an outer surface, with a plurality of interlocking teeth positioned on the outer surface. The valve assembly further includes a valve base. The valve base having a base flange attachable to a flexible bag, and a upstand portion extending upwardly therefrom defining an inner surface and an outer surface. The inner surface having a plurality of seal beads extending therearound, and the outer surface having a plurality of teeth positioned thereon. The upstand portion insertable into the base receiving channel of the valve housing. Upon insertion, the plurality of seal beads sealingly engaging the inner surface of the base channel, and the interlocking teeth of the base channel interlocking with the teeth of the outer surface of the upstand portion, to in turn, couple the valve base to the valve housing.

In some configurations, the central web includes an inner surface facing the first valve side and an outer surface facing the second valve side. The outer surface includes a central peak and an annular valley surrounding the central peak. The outer rim extends beyond the annular valley toward the upper end.

In some configurations, the outer rim includes an upper end, wherein the upper end of the rim defines a height that corresponds to the central peak.

In some configurations, the central web has a substantially uniform thickness between the annular valley and the central peak.

In another aspect of the disclosure, the disclosure is directed to a valve assembly. The valve assembly comprises a valve housing and a valve body. The valve housing has a lower end and an upper end. A valve seat is positioned therebetween. The valve seat being inclined inwardly toward the lower end. The valve body is pivotably positionable within the valve housing, and pivots between a first closed orientation and a second open orientation. The valve body is pivotable about an axis that extends through the valve housing positioned between the upper end and the valve seat. In the first closed orientation, the valve body is configured to translate toward and away from the lower end of the valve housing.

In some configurations, the valve body further includes an outer rim with a seal extending along the outer rim. The seal is configured to sealingly engage the valve seat. The seal biases the valve body toward the upper end of the valve housing in the first closed orientation.

In some configurations, the valve body further includes an outer surface facing the upper end in the first closed orientation. The valve body includes an outer rim and a central web. The outer rim extends beyond the central web toward the upper end. The central web includes a central peak extending toward the upper end and an annular valley extending therearound between the central peak and the outer rim.

In some configurations, the valve body further includes a plurality of spaced apart seals along the valve body, each of the spaced apart seals engaging the valve seat in the first closed orientation.

The disclosure is likewise directed to methods of utilizing the valve assembly of the present disclosure, including methods of sterilizing the valve assembly and filling and dispensing flowable material therefrom.

BRIEF DESCRIPTION OF THE DRAWINGS

The disclosure will now be described with reference to the drawings wherein.

DETAILED DESCRIPTION OF THE DISCLOSURE

Figure 1:
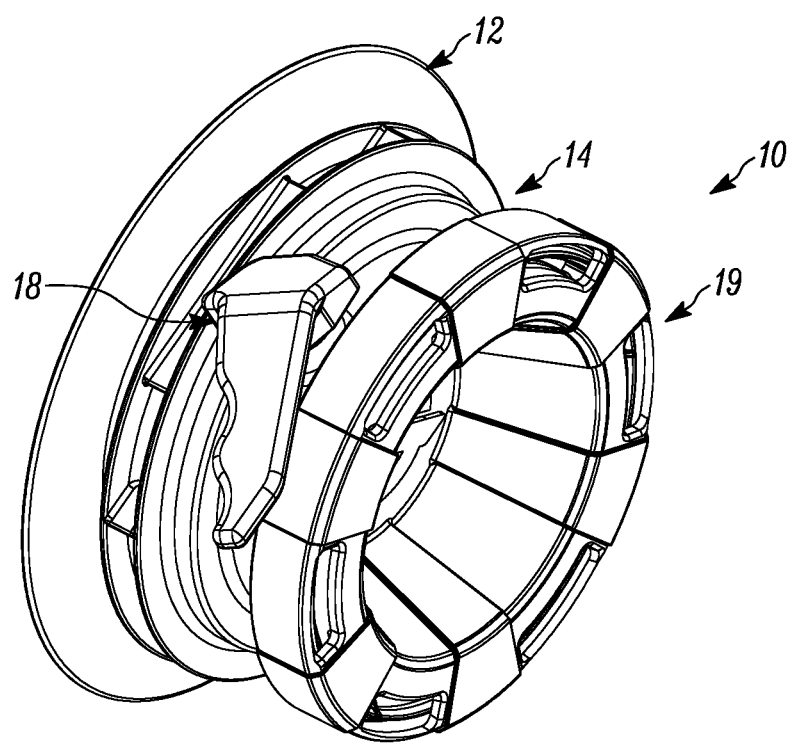
FIG. 1 of the drawings is a front perspective view of the valve assembly of the present disclosure.

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Figure 2:
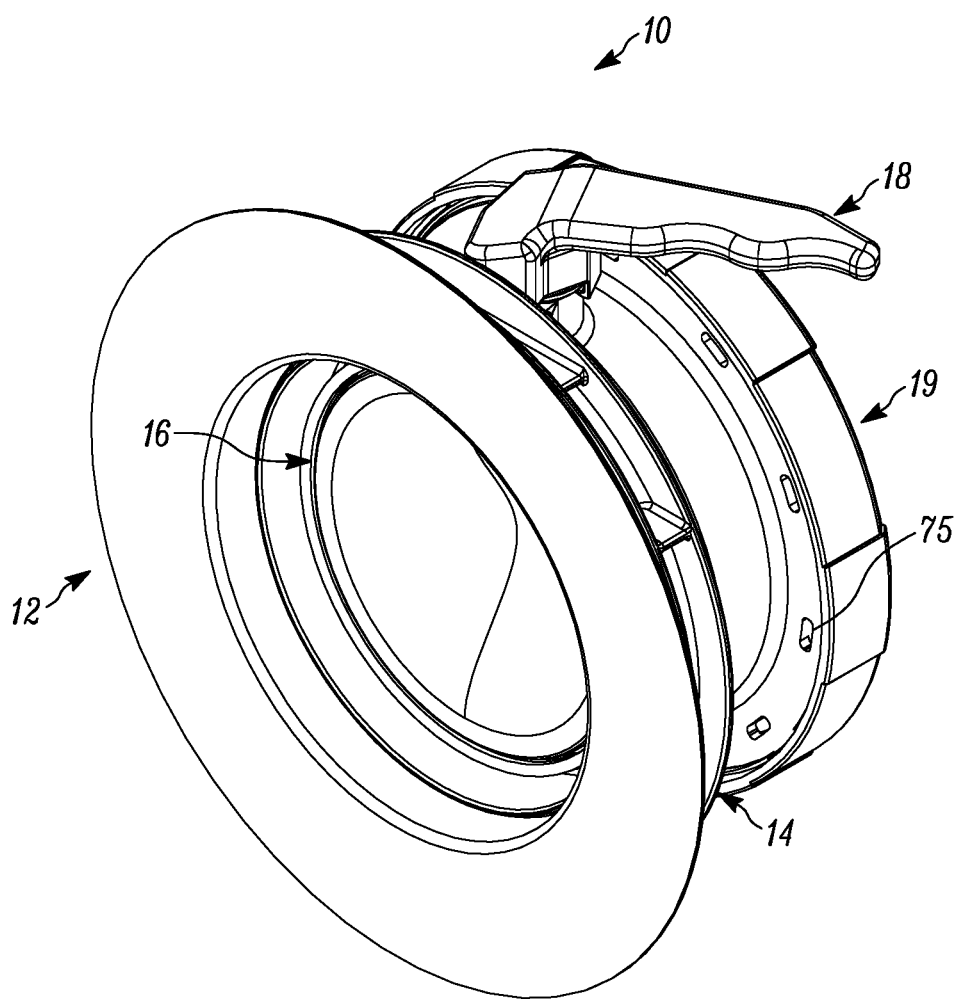
FIG. 2 of the drawings is a back perspective view of the valve assembly of the present disclosure.
Figure 3:
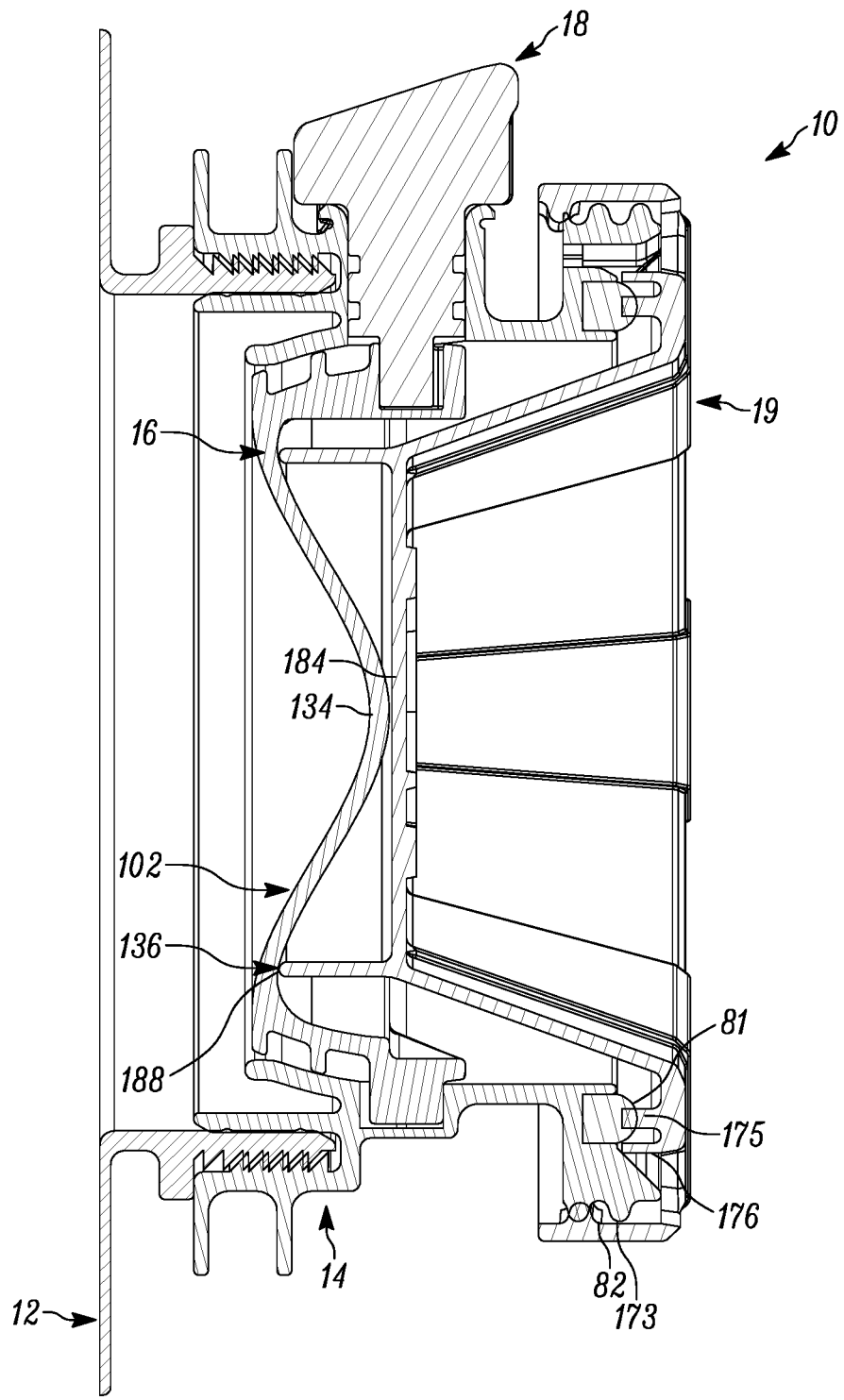
FIG. 3 of the drawings is a cross-sectional view of the valve assembly of the present disclosure.

Referring now to the drawings and in particular to FIGS. 1, 2 and 3, collectively, the valve assembly is shown generally at 10. The valve assembly 10 includes valve base 12, valve housing 14, valve body 16 and handle 18. The valve assembly 10 is configured to be coupled to a flexible package (typically formed from a plurality of walls that are joined together through a plurality of seals). While certainly not limited thereto, the valve assembly is well suited for use in association with the dispensing of flowable material (such as liquids, purees and syrups), including but not limited to foodstuffs, in an aseptic environment. Such an environment often requires the steam sterilization of the valve assembly. The valve assembly is particularly well suited to maintaining integrity and the like in such steam sterilization processes.

Figure 4:
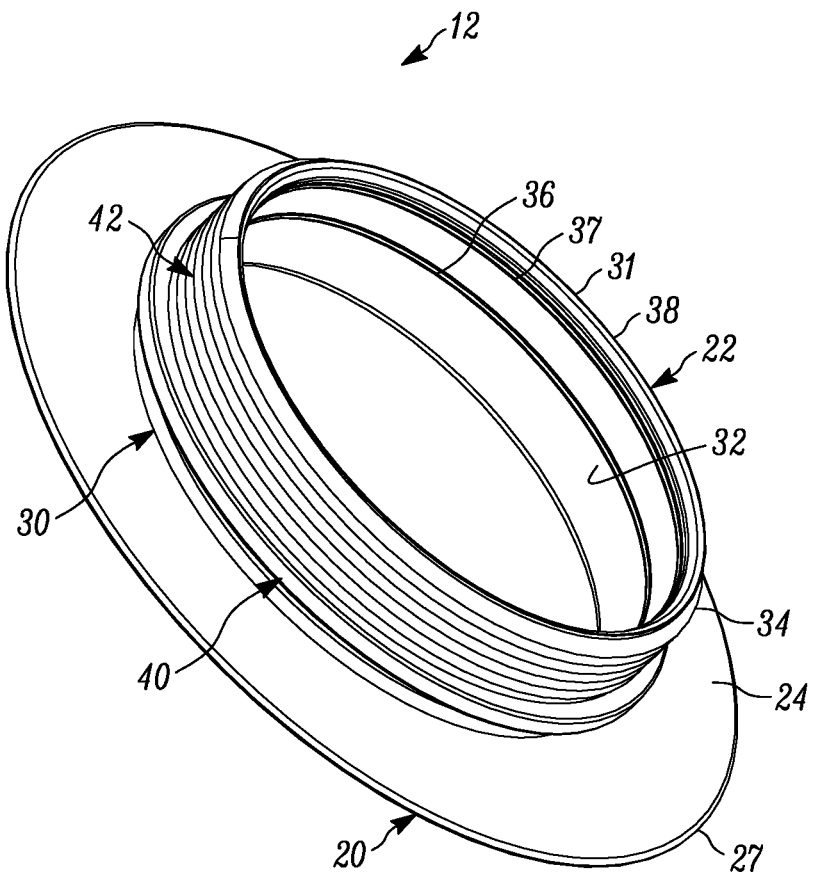
FIG. 4 of the drawings is a perspective view of the valve base of the valve assembly of the present disclosure.
Figure 5:
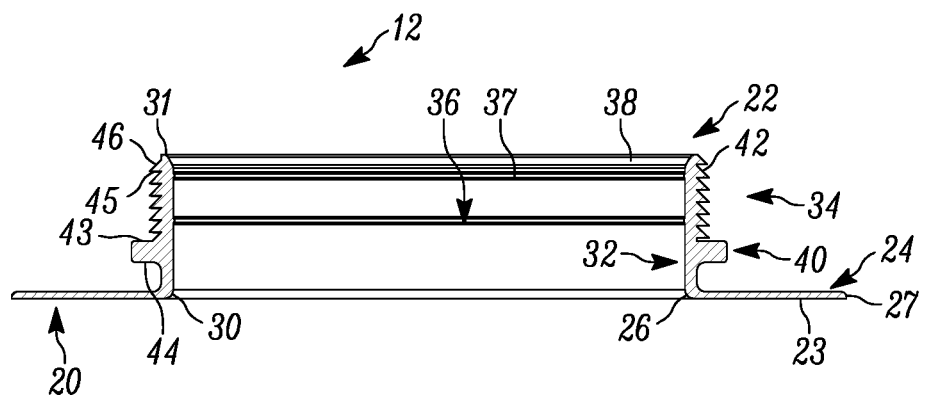
FIG. 5 of the drawings is a cross-sectional view of the valve base of the valve assembly of the present disclosure.

The valve base 12 is shown in greater detail in FIGS. 4 and 5 as comprising base flange and upstand portion. It will be understood that the valve base 12 is configured to interface with the flexible bag. The base flange 20 includes upper surface 24, lower surface 25, proximal edge 26 and distal edge 27. The base flange 20, in the configuration shown, is substantially uniform in thickness and is of a generally planar configuration. Of course, variations are contemplated to the thicknesses and the overall configuration of the base flange. The valve base comprises a polymer based material, including but not limited to polypropylene, polyethylene, and nylon, among others.

The upstand portion 22 extends from the base flange in a direction away from the upper surface 24 thereof. The upstand portion extends around the distal edge 27 and the opening defined thereby so as to define an opening (in the configuration shown, a cylindrical opening). The upstand portion 22 extends from proximal end 30 (which meets the proximal edge 26) to distal end 31. The upstand portion includes inner surface 32 and outer surface 34. The inner surface includes first seal bead 36 and second seal bead 38 which comprise generally semi-circular protrusions extending inwardly from the inner surface 32.

Figure 14:
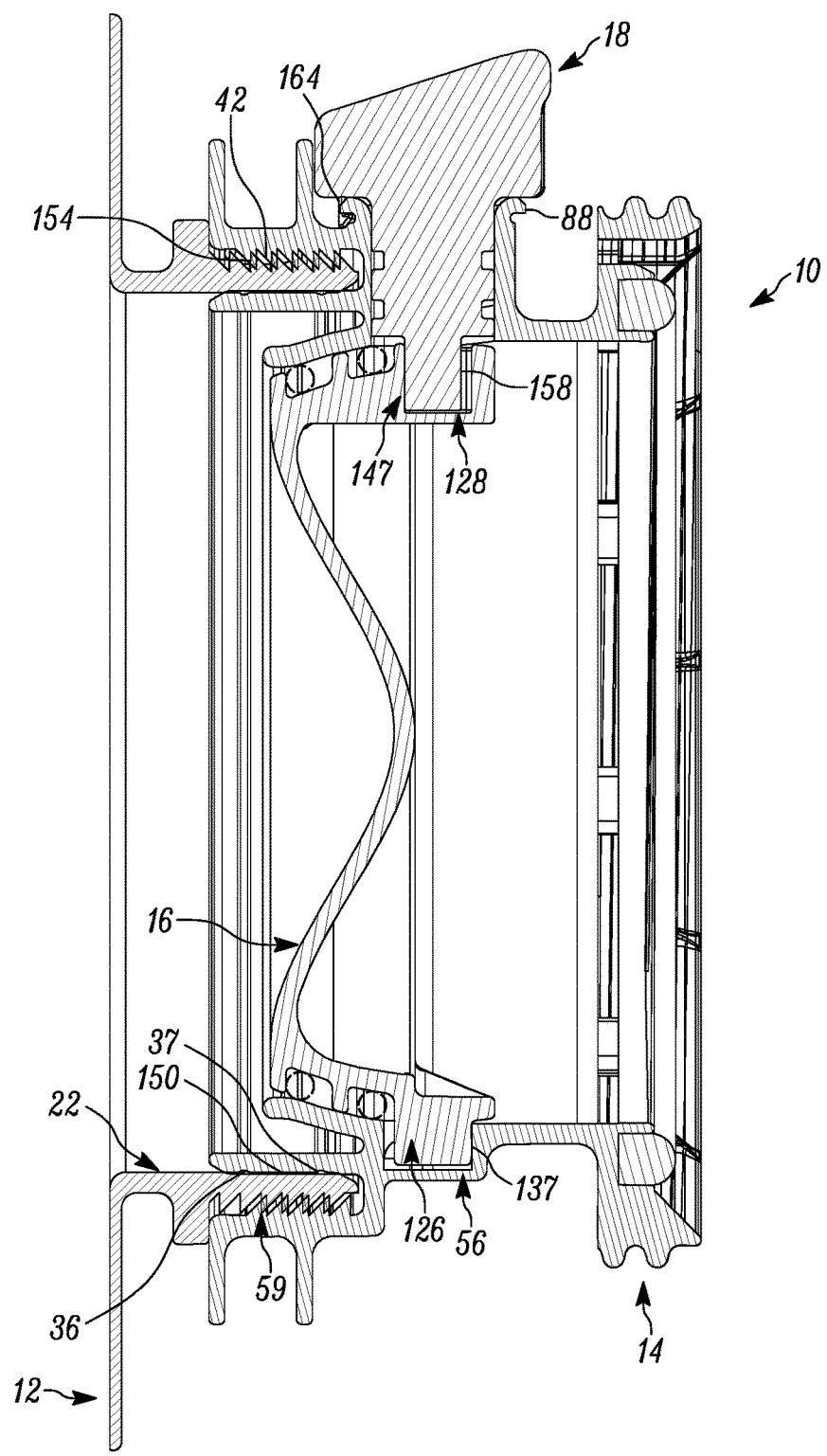
FIG. 14 of the drawings is a cross-sectional view of the valve assembly with the cap member removed, showing, in particular, the valve body in the first closed orientation, with the O-rings directing the valve body toward the upper end of the valve housing.
Figure 15:
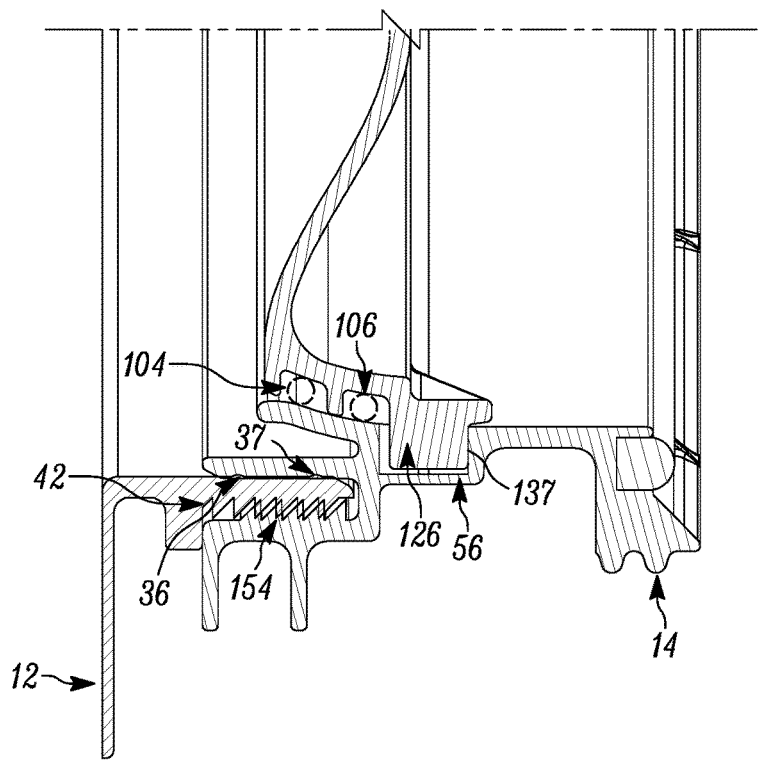
FIG. 15 of the drawings is a partial cross-sectional view of the valve assembly with the cap member removed, showing, in particular, the resilience of the O-rings directing the valve body toward the upper end of the valve housing, and, the valve axle slot having the first axle protrusion extending thereinto and being directed at the upper end of the slot.
Figure 16:
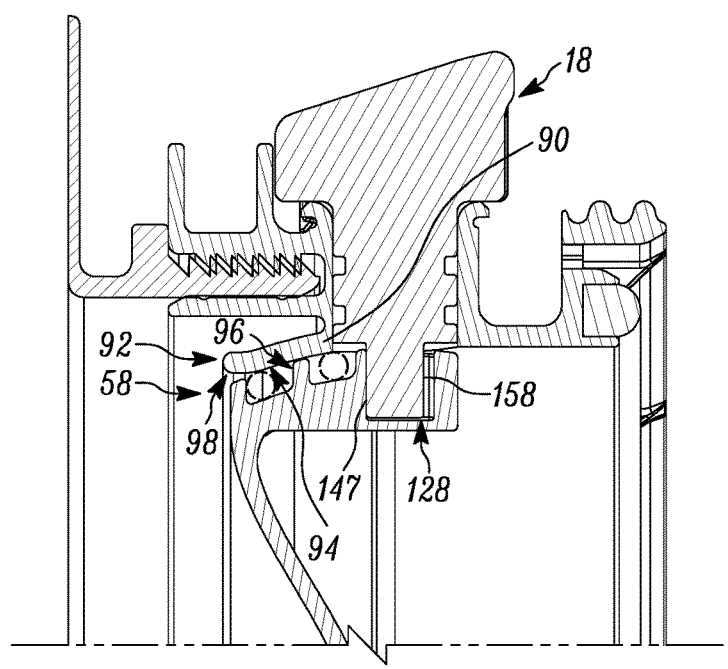
FIG. 16 of the drawings is a partial cross-sectional view of the valve assembly with the cap member removed, showing, in particular, the resilience of the O-rings directing the valve body toward the upper end of the valve housing, and, the valve axle slot having the axle member of the handle extending into the second axle slot of the valve body and being directed at the lower end of the second axle slot.

The outer surface 34 includes lower flange 40 and interlocking teeth 42. The lower flange 40 includes upper surface 43 and outer surface 44. The interlocking teeth 42, in the configuration shown, have substantially uniform configurations, each having an upper surface 46 and a lower surface 45. The upper surface is angled in the downward direction toward the lower flange 40 with the lower surface 45 being substantially parallel to the lower flange and substantially perpendicular to the outer surface of the upstand portion. It will be explained below, and as is shown in FIG. 14 through 16, that the interlocking teeth 42 interface with mating structures within the base receiving channel 59 of the valve housing 14.

Figure 6:
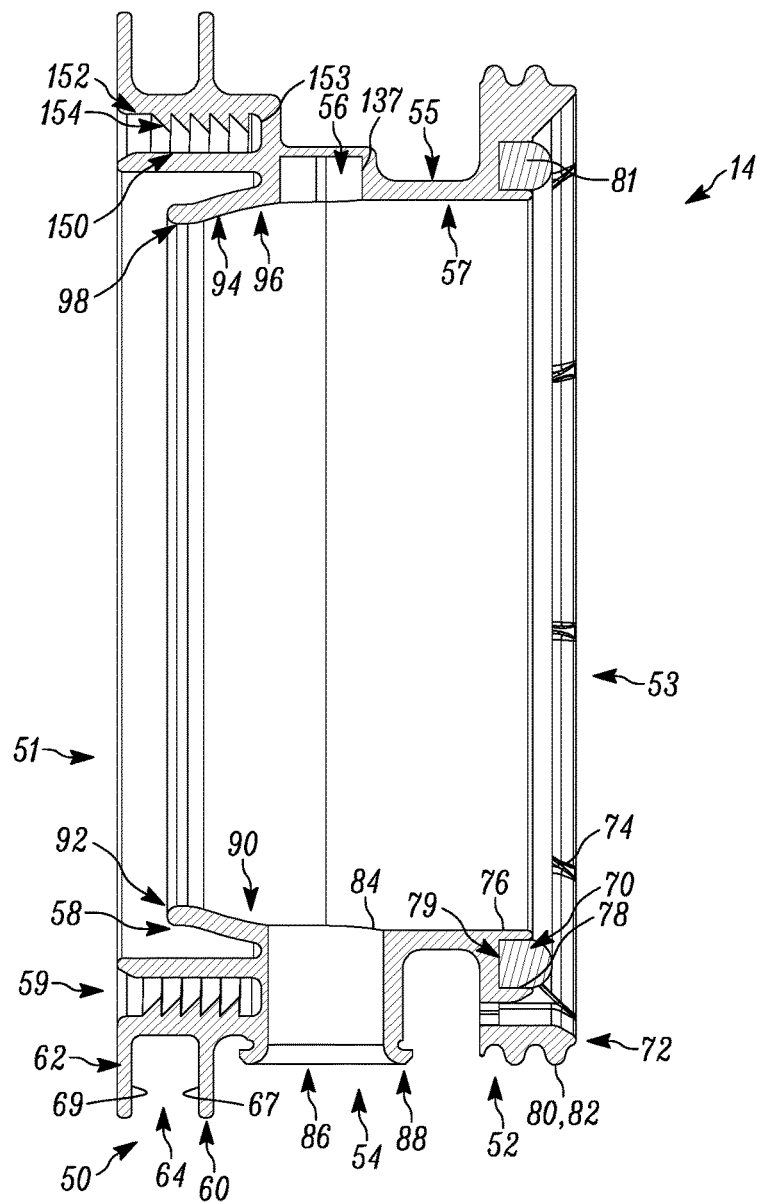
FIG. 6 of the drawings is a cross-sectional view of the valve housing of the valve assembly of the present disclosure.
Figure 7:
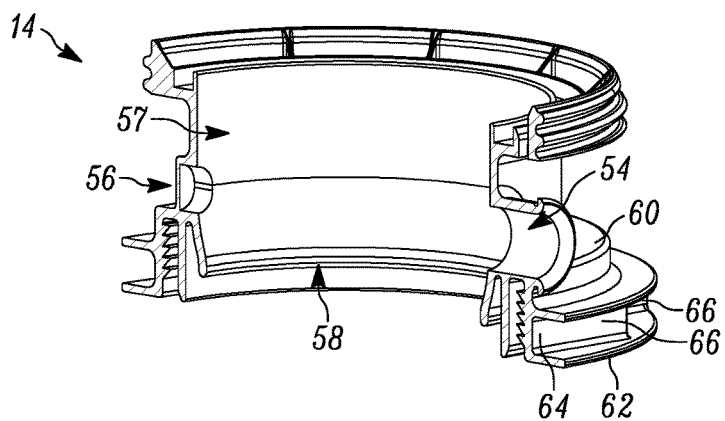
FIG. 7 of the drawings is a cross-sectional perspective view of the valve housing of the valve assembly of the present disclosure.

The valve housing 14 is shown in FIGS. 6 and 7 as comprising lower flange assembly 50, upper flange 52, transverse handle opening 54, valve axle slot 56, valve seat 58 and base receiving channel 59. The valve housing 14 includes lower end 51, upper end 53, outer surface 55 and inner bore 57. The valve housing is formed from a polymer material, including, but not limited to polypropylene, polyethylene and nylon, among others.

The lower flange assembly 50 includes first flange 60 and second flange 62. The first flange 60 includes bottom surface 67 and the second flange 62 includes top surface 69. A slot 64 is defined between the two flanges, by the bottom surface 67 of the first flange, and the top surface 69 of the second flange. A plurality of transverse webs, such as transverse web 66 extends between the first and second flanges. In the configuration shown, the first and second flanges are substantially parallel to each other and substantially perpendicular to the inner bore of the valve housing 14. In the configuration shown, the first and second flanges have substantially the same diameter and substantially the same thickness. Of course, variations are likewise contemplated. The transverse webs that extend between the first and second flanges are configured to receive and matingly engage with different tools, filling and/or dispensing equipment and the like.

The upper flange 52 includes inner portion 70, outer portion 72, and webs, such as web 74. The webs 74 extend radially outwardly to couple the inner portion 70 to the outer portion 72. The webs 74 are spaced apart radially at predetermined intervals with respect to each other, defining openings 75 (FIG. 2) therebetween. The inner portion of the upper flange 70 includes inner wall 76 and outer wall 78. The inner wall 76 forms the inner bore 57. The outer wall 78 is radially outward of the inner wall 76, forming a generally uniform annular channel 79 therebetween. In the configuration shown, the annular channel 79 is of substantially uniform depth, and configured to receive and retain an seal member therein. One such seal is shown in FIG. 6 with the reference number 81. The seal 81 is shown as having a substantially D-shaped cross-sectional configuration.

The outer portion 72 is shown in FIG. 6 as comprising outer surface 80 having threads thereon. In the configuration shown, the outer portion 72 extends beyond the upper end of the inner bore 57, with the webs 74 extending therebetween being angled and increasing radially outward in depth, so as to form an inclined surface that extends from the inner portion 70 to the outer portion 72. In the configuration shown, the first and second flanges of the lower flange assembly 50 extend radially outwardly beyond the upper flange so as to define the footprint of the valve housing.

The transverse handle opening 54 together with the valve axle slot 56 define an axis of rotation of the valve body 16, and are, therefore positioned on opposite sides of each other about the valve housing with the axis extending generally through the center of the circular cross-sectional configuration of the valve housing inner bore 57 (thereby defining a diameter). The transverse handle opening comprises a generally cylindrical opening having an inner end 84 and an outer end 86. In the configuration shown, the generally cylindrical opening defines a bore of substantially uniform circular cross-sectional configuration. A outer rim 88 extends about the outer end 86, and is configured to provide a sealing engagement with the handle.

The valve axle slot 56 comprises a generally circular, but elongated slot, that is elongated in a direction that is parallel to the axis of the inner bore 57 and generally perpendicular to the upper and lower end of the valve housing. The valve axle slot, it will be explained, provides for an axis of rotation of the valve body, while allowing the valve axle to move toward and away from the lower end of the valve upon an application of force against the valve body. Preferably, the valve axle slot extends into the inner bore while not extending through to create an opening to the outer surface. Such a configuration precludes the need to have a sealing surface to preclude egress from the valve.

The valve seat 58 is shown as comprising proximal end 90, distal end 92 and seat surface 94. The valve seat 58 comprises a protrusion that extends inwardly from the inner bore in a generally conical configuration inwardly and toward the lower end thereof. The conical configuration includes an inclined portion 96 starting at the proximal end and a parallel portion 98 at the distal end thereof. The transition from the inclined portion 96 to the parallel portion occurs at or beyond the upper channel 122 of the outer surface of the valve body outer rim 100. A tapered slot is defined between the back wall of the valve seat and the inner bore 57. In other embodiments, the thickness or the configuration of the inner bore may be adjusted to taper, instead of including a valve seat in the form of an inwardly directed appendage from the inner bore of the valve housing.

The base receiving channel 59 is shown in FIG. 6 as comprising inner surface 150 and outer surface 152 with a base wall 153. A plurality of interlocking teeth, such as interlocking tooth 154, extend into the channel from the outer surface 152. As will be understood the base receiving channel 59 shape matingly engages the upstand portion 22 of the valve base. More particularly, and as will be described below, and with reference to FIGS. 14 through 16, the upstand portion 22 extends into the base receiving channel 59 so that the inner surface 150 engages with the first and second seal beads 36, 37 of the inner surface 32 of the upstand portion, while the interlocking teeth 42 of the outer surface of the upstand portion interface with the interlocking teeth 154 of the outer surface of the base receiving channel. Such an interface produces a fluid-tight seal between the members (with portions of the flexible bag being positioned therebetween).

Figure 8:
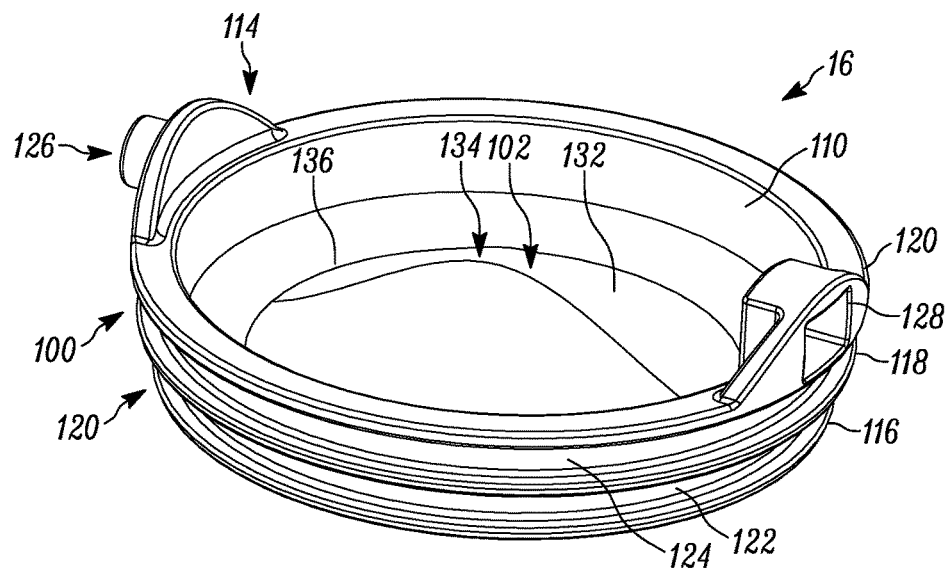
FIG. 8 of the drawings is a perspective view of the valve body of the valve assembly of the present disclosure.
Figure 9:
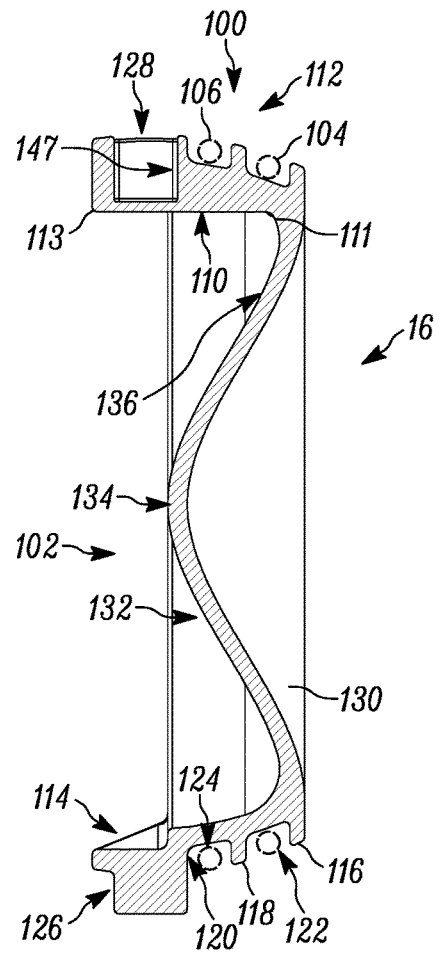
FIG. 9 of the drawings is a cross-sectional view of the valve body of the valve assembly of the present disclosure.
Figure 10:
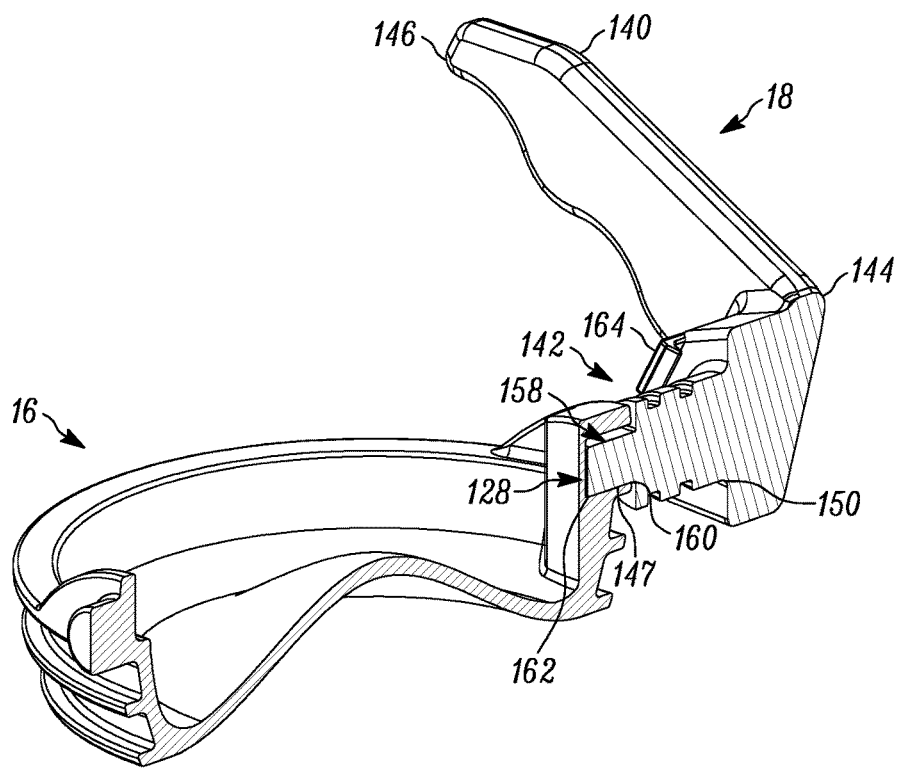
FIG. 10 of the drawings is a cross-sectional perspective view of the valve body and the handle of the valve assembly of the present disclosure.

With reference to FIGS. 8 through 10, the valve body 16 includes outer rim 100, central web 102, first O-ring 104 and second O-ring 106. The valve body 16 is pivotally positioned within the inner bore of the valve housing, so that the valve body can sealingly engage the valve seat 58 thereof, with the valve body pivoting about the axis created by the transverse handle opening and the valve axle slot. Additionally, the valve body is configured to translate along (or displace between) the valve housing between the upper and lower ends thereof, upon the direction of a force (or pressure) in the valve body on one side of the valve housing.

The outer rim 100 includes inner surface 110, outer surface 112 and rotational axis assembly 114. The outer rim includes lower end 111 and upper end 113 which generally defines the inner and outer surfaces, with the rotational axis assembly extending from the upper end 113 away from the lower end 111. The upper and lower ends generally defining a circular configuration that substantially matches that of the inclined portion 96 of the valve housing. The inner surface in the embodiment shown comprises a curved wall that preferably substantially matches the shape of the inclined portion 96 of the valve housing. The outer surface 112 likewise preferably substantially matches the shape of the inclined portion 96 and includes upper flange 116, central flange 118 and lower flange 120. The three flanges are substantially parallel to each other and spaced apart from each other so as to define channels therebetween. In particular, the upper channel 122 is defined by the upper flange and the central flange. The lower channel 124 is defined by the central flange 118 and the lower flange 120. The first O-ring 104 extends into the upper channel 122 and the second O-ring 106 extends into the lower channel 124. The O-rings and the channels are configured such that the O-ring extends upwardly beyond the channel and the flanges. While not required, due to the configuration of the channels and the flanges, the channels have different slopes such that each of the O-rings is positioned along a different slope. In such a configuration, the two O-rings are isolated from each other, and fluid on one side of the O-ring (and temperature) is isolated from the second O-ring. It will be understood that in other configurations, a single channel may be defined between a pair of spaced apart flanges. Many of the advantages of the configuration of the valve are realized with the use of only a single O-ring in the place of a pair of spaced apart O-rings.

The rotational axis assembly 114 includes first axle protrusion 126 and second axle slot 128, which are positioned on opposite sides of each other defining an axis of rotation that preferably extends through the center of the valve body. The first axle protrusion generally shape-matingly fits into and rotates within the valve axle slot 56. In addition, the first axle protrusion can slidably translate within the valve axle slot 56 toward or away from the lower end of the valve housing. The second axle slot 128 comprises a generally circular slot that is elongated, much like the valve axle slot 56. As will be explained, the portion of the axle member 158 of the shaft 142 of the handle 18 is configured to both rotate and slidably translate within the second axle slot 128 of the valve body 16. It will be understood that the relationship between valve axle slot 56 and the second axle slot 128 is such that when the valve body is in a closed orientation against the valve housing, the two axle slots are aligned so as to permit the valve body to move relative to the valve housing in a substantially uniform manner (wherein the valve body can move generally perpendicular to the axis of the inner bore). Such a configuration generally minimizes the possibility of angular displacement and moments on the valve body that can lead to unintended stresses, and, in turn, leaking and the like.

The central web 102 is shown in FIGS. 8 through 10 as comprising inner surface 130, outer surface 132. In the configuration shown, the central web has a substantially uniform thickness, with the inner and outer surfaces being substantially equally spaced apart from each other. The outer surface 132 is substantially outwardly convex and includes a central peak 134 surrounded by an annular valley formed between the central web and the inner surface 110 of the outer rim 100. The central peak 134 has an amplitude that matches the upper end 113 of the outer rim 100, although it is contemplated that the amplitude may be greater or smaller than the upper end 113 of the outer rim 100.

Figure 11:
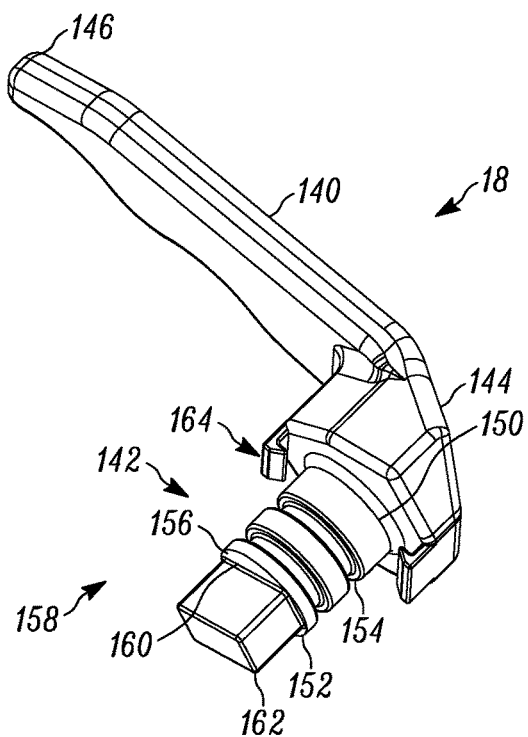
FIG. 11 of the drawings is a perspective view of the handle of the valve assembly of the present disclosure.

The handle 18 is shown in FIGS. 10 and 11 as comprising lever arm 140 and shaft 142. The lever arm 140 includes proximal end 144 and distal end 146. It will be understood that the lever arm is configured for the manual grasping and rotation by a user. The handle is coupled to the valve such that rotation of the lever arm controls the position of the valve body within the valve housing (i.e., open, closed, partially open, etc.). In the configuration shown, the lever arm 140 is configured to rotate through an arcuate distance of approximately 90° to effectuate the valve body between an open and a closed position. The lever arm may have protrusions and shapes that limit the rotation thereof relative to the housing by interfering with portions of the housing, such as the lower flange assembly, for example.

The shaft 142 extends generally perpendicularly from the lever arm 140 and includes first end 150 and second end 152. An inner face is positioned at the second end thereof, with an axle member 158 extending outwardly therefrom. The shaft 142 is generally cylindrically shaped so as to engage within the transverse handle opening 54, with the first end generally being positioned at the outer end, and the deflectable outer rim 88, and the second end corresponding to the inner end 84 of the opening 54. In the configuration shown, a pair of annular slots are positioned about the shaft in a spaced apart orientation. The annular slots are configured to receive O-rings or other sealing members so as to preclude the passage of fluid (i.e., steam, air, flowable material, etc.) therethrough.

Additionally, the handle 18 includes locking arms 164 on opposing sides of the shaft 142. The locking arms 164 interface with the deflectable outer rim 88 so as to lock the handle relative to the valve body 16, to preclude the separation of the components due to the pressure or temperature exertions on the handle 18 (FIG. 14).

The axle member 158 includes a first end at the inner face 156 and a second end 162 spaced therefrom. The axle member defines a cross-sectional configuration that allows for imparting rotation to the valve body upon rotation of the lever arm, while also allowing for the translation of the valve body relative to the axle member 158 at least when the valve is in the closed orientation. It will be understood that while the first axle protrusion 126 of the valve body 16 rotates within the valve axle slot 56 at one end, the axle member 158 of the handle rotates with the second axle slot. Yet, both slots allow for the slidable movement of the respective axle when within the slot. It will be understood that due to the movement, when in the closed position, and without any application of force, the resilience of the O-rings 104 and/or 106 will force the valve body into a position wherein the first axle protrusion is directed toward the upper end 137 of the valve axle slot 56, while the axle member 158 is directed toward the lower end 147 of the second axle slot 128.

Figure 12:
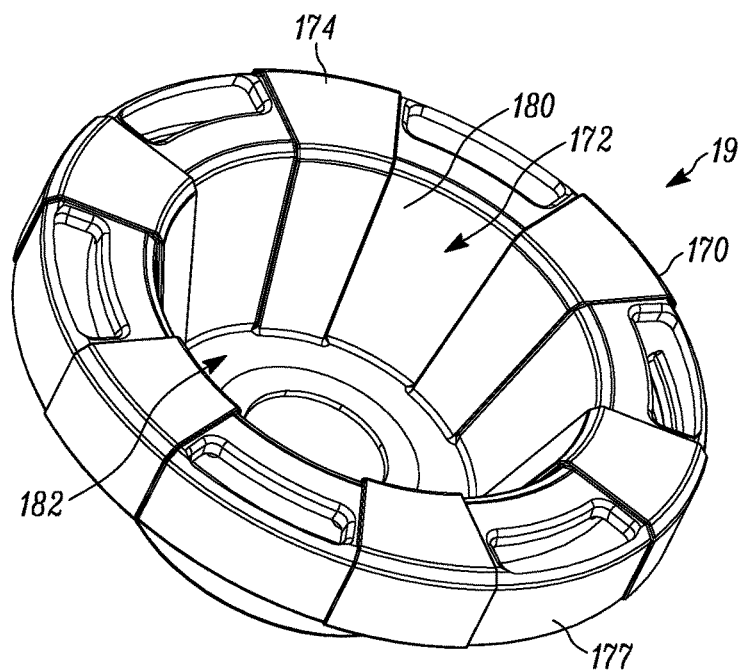
FIG. 12 of the drawings is a perspective view of the cap member of the valve assembly of the present disclosure.
Figure 13:
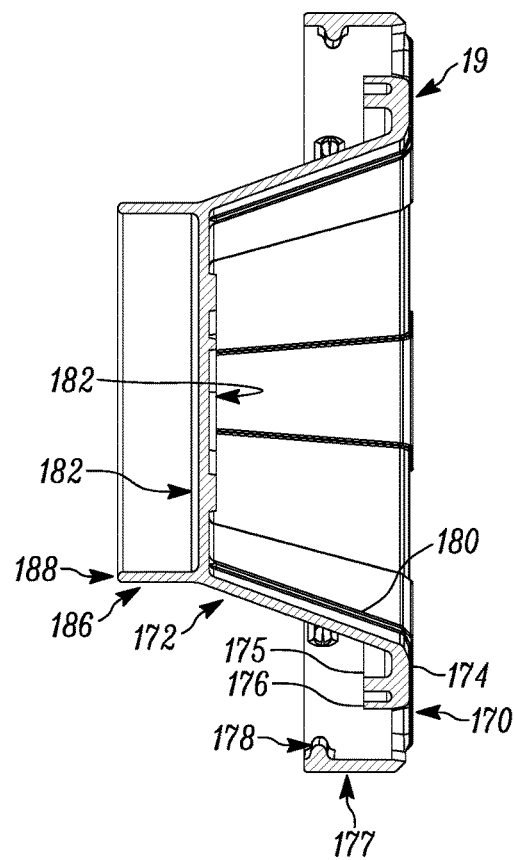
FIG. 13 of the drawings is a cross-sectional view of the cap member of the valve assembly of the present disclosure.

With reference to FIGS. 12 and 13, the valve may further include cap 19 which is configured to cover the second side of the valve prior to use. The cap 19 includes outer rim 170 and central body 172. The outer rim 170 includes top surface 174, inner depending seal 175, outer depending seal 176, and depending skirt 177. The top surface of the outer rim is generally substantially planar and extends over the upper end of the valve housing 14, substantially encasing the upper flange 52.

The central body 172 of the valve cap 19 includes depending wall 180, base 182 and base skirt 186. The depending wall tapers inwardly toward the valve body 16, and also inwardly away from the inner bore 57, defining a generally conical configuration. The base 182 is generally planar and generally parallel to the top surface 174. The base includes lower surface 184 which spans the base 182. The depending skirt extends annularly about the outer perimeter of the base 182, and includes bottom ring 188 which defines the lower extremity of the cap 19.

With reference to FIG. 3, in the capped orientation, the cap can be threaded utilizing the thread 178 co-acting with the threads 82. As the cap is threaded onto the valve housing, the inner depending seal 175 and the outer depending seal 176 approach the upper flange. The inner depending seal 175 interfaces and sealingly engages the seal 81 positioned within the annular channel 79. The outer depending seal 176 interacts with the inner portion of the upper flange and the seal 81 as well, to essentially sealingly isolate the second side of the valve body from the outside elements.

At the same time, as the cap is threaded, the lower surface 184 interfaces with the central peak 134 of the central web 102 of the valve body 16. Additionally, the bottom ring 188 interfaces with the surrounding annular valley 136 of the central web 102 of the valve body 16. As such, the cap 19 provides a lock on the valve body which precludes rotation of the lever arm of the handle, and the movement of the valve body out of the closed configuration. Furthermore, the cap includes, preferably, only the top surface 174 which extends beyond the upper end of the valve housing, thereby limiting the additional build height to the valve when capped. Furthermore, an integrated tamper evident feature can be incorporated into the valve cap, to indicate that the valve cap has been previously removed or that tampering has occurred.

The assembled valve body and valve housing is first provided. As is shown in FIG. 1, the valve body is initially in the closed orientation. In such an orientation, the lever arm is precluded from further movement by the lower flange assembly 50. The first O-ring 104 and the second O-ring 106 contact the seat surface 94 of the valve seat 58, providing a fluid-tight closure between a first side of the valve (which is defined by the valve housing between the lower end and the valve body) and a second side of the valve (which is defined by the valve housing between the upper end and the valve body). As explained above, the natural resiliency of the O-rings directs the valve body toward the upper end of the valve housing, forcing the first axle protrusion against the upper end 137 of the valve axle slot 56, and forcing the axle member 158 against the lower end 147 of the second axle slot.

The user can assemble the valve body 14 onto the valve base 12. When the body and the base are joined, the upstand portion 22 of the valve base is directed into the base receiving channel 59 of the valve housing. A seal is formed between the first and second seal beads 36, 37 of the inner surface 32 of the upstand portion 22 and the inner surface 150 of the base receiving channel 59. At the same time, the interlocking teeth 42 of the outer surface of the upstand portion are directed past and, into engagement with the interlocking teeth 154 of the outer surface of the base receiving channel. The two structures click past each other until the distal end of the upstand portion interfaces with the base wall 153, and/or the bottom surface 67 of the first flange 60 contacts the upper surface 43 of the lower flange 40. Advantageously, the predominant thrust of the sealing function is effectuated by the interface of the seal beads of the inner surface of the upstand portion against the inner surface of the base receiving channel, while the predominant thrust of the retaining function is effectuated by the interface between the locking teeth. Separating the sealing function and the retaining function achieves a more robust interlock between the valve base and the valve body. In addition, a coupling that is preferably free of elastomers and/or threading can be achieved, as well as an aseptic closure.

It will be understood that the flexible bag is coupled to the valve housing (or sandwiched between the valve housing and the valve base). A flowable material may be placed within the flexible bag. The flowable material extends into the first side of the valve which is bound by the first O-ring 104. Passage therebeyond is precluded. As is often the case, it may become necessary to sterilize the second side of the valve prior to dispensing (or prior to filling in some instances). To achieve the same, the upper end of the valve housing may be coupled to a steam sterilization unit which applies steam at an elevated pressure into the second side of the valve so as to sterilize the second side of the valve.

Figure 17:
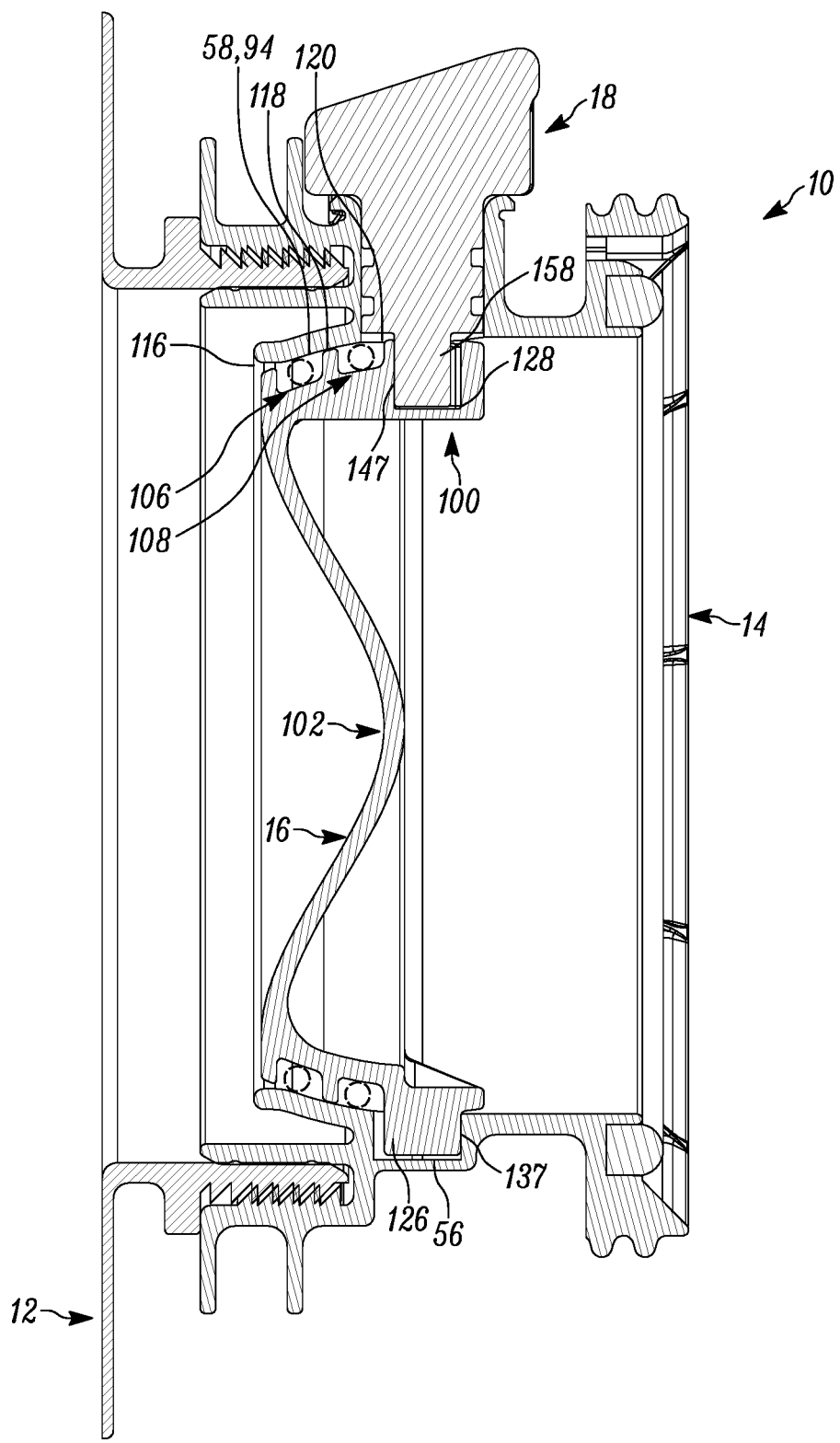
FIG. 17 of the drawings is a cross-sectional view of the valve assembly with the cap member removed, showing, in particular, a force (for example, due to application of steam sterilization) imparted onto the valve body, and the translation of the valve body toward the lower end of the valve body, forcing the outer rim of the valve body toward the valve seat and compressing the O-rings sufficient to have contact between the outer rim and the valve seat.

With reference to FIG. 17, when a predetermined pressure is applied to the second side of the valve, the resilience of the O-rings 104, 106 is exceeded and the valve body is translated toward the lower end of the valve housing 14. In other words, the first axle protrusion 126 translates along the valve axle slot 56 away from the upper end 137, and the axle member 158 translates along the second axle slot 128 away from the lower end 147. As the steam pressure increases, the O-rings 104, 106 are compressed such that the upper flange 116, central flange 118 and/or lower flange 120 is pressed against the seat surface 94 of the valve seat 58. In addition, due to the configuration of the central web 102, the pressure is deflected by the central peak toward and into the central valley in an outward direction, which outwardly directs the outer rim 100 toward the seat surface 94.

Eventually, the second side of the valve is exposed to steam at the correct pressure and temperature for the appropriate time. As the steam pressure is reduced, the resilience of the O-rings 106, 108 overcomes the pressure on the second side of the valve and pushes the valve body toward the upper end, translating the valve until the upper end 137 of the valve axle slot 56 is contacted by the first axle protrusion, and the lower end 147 of the second axle slot 128 is reached by the axle member 158.

While various different exposure to steam is contemplated, it is contemplated that the steam is generally applied according to certain specifications. For example, at 121° C. typically the steam is applied for 15 minutes (although in practice users often vary between 10 and 30 minutes). At a steam temperature of 130° C., typically the steam is applied for 2.5 minutes (although in practice users often vary between 3 and 5 minutes). At a steam temperature of 140° C., typically the steam is applied for 0.9 seconds (although in practice users often vary between 5 and 30 seconds). Of course, these temperatures and times are considered exemplary, and not limiting. That is, other temperatures, pressures, medium other than steam sterilization, and times, amongst other parameters is likewise contemplated.

Figure 18:
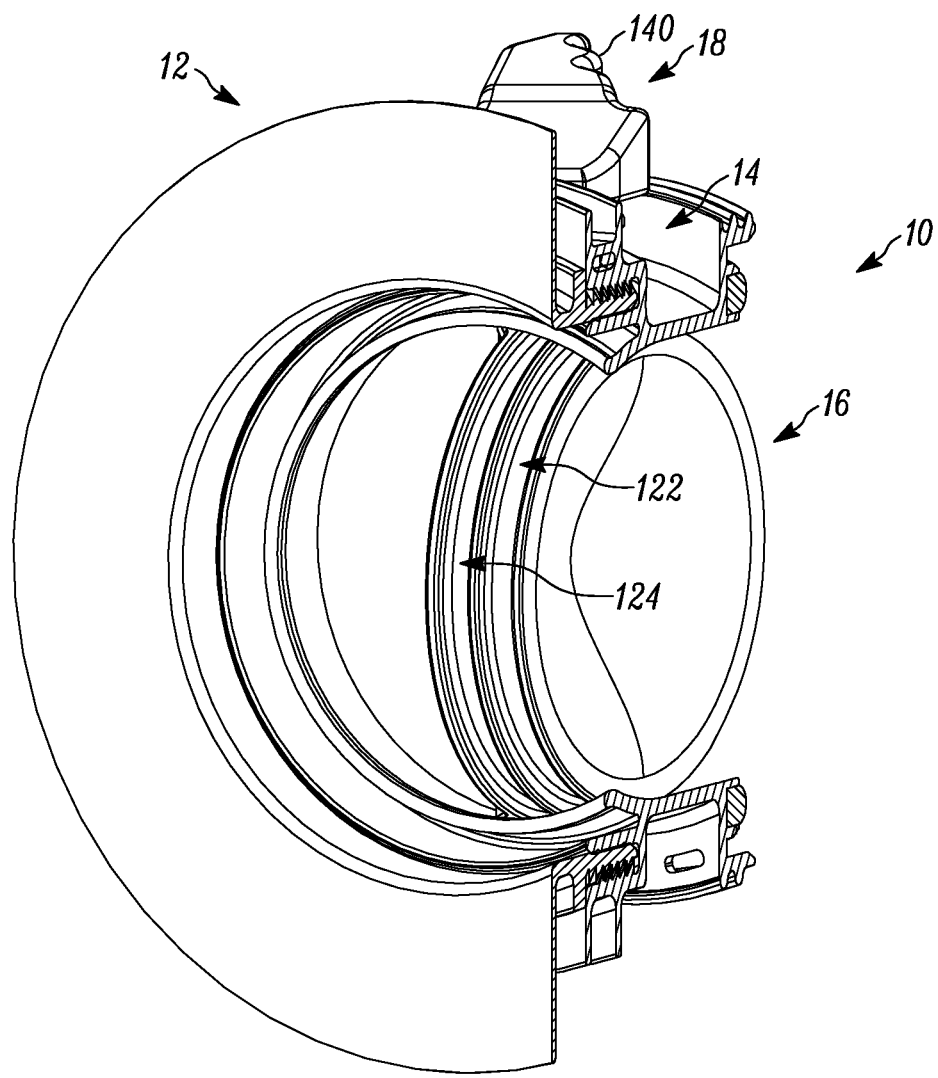
FIG. 18 of the drawings is a cross-sectional view of the valve assembly with the cap member removed, showing, in particular, the valve body in the second open orientation.

With reference to FIG. 18, to open the valve, the user grasps the lever arm 140 and rotates the lever arm relative to the valve housing 14. The rotation of the lever arm rotates the valve body about the axis defined by the first axle protrusion and the axle member (in cooperation with the shaft of the handle 18). It will be understood that the upper and lower channels 122, 124 of the outer rim are spaced apart from the axis of rotation of the valve body toward the lower end of the valve housing. As a result, the O-rings are predominantly separated from the valve seat so as to limit any contact therebetween in the open configuration. Additionally, by positioning the axis of rotation spaced apart from the valve seat in a direction away from the lower end, the valve can minimize the gap between the valve base and the valve. It will be understood that the handle is preferably configured to interfere with portions of the valve housing 14 when the desired end of travel into the open position is reached. In the configuration shown, the handle 18 interferes with the lower flange assembly in the fully open configuration. The same procedure, followed in reverse, can be initiated and completed to direct the valve from the open configuration to the closed configuration.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A valve assembly comprising:
   a valve housing having a lower end and an upper end, and defining an inner bore, the valve housing including a valve seat spaced apart from the lower end and the upper end, separating the valve housing into a first valve side and a second valve side, the valve seat defining a seat surface that is inclined inwardly and toward the lower end of the valve housing;
   a valve body including an outer rim with an outer surface and a central web spanning therebetween, the outer rim including at least two spaced apart outwardly directed annular flanges defining at least one channel therebetween, and a seal positioned within the at least one channel, the outer rim inclined outwardly so as to correspond to the seat surface, with the valve body further having an axis of rotation that extends transversely through the valve body spaced apart from the annular flanges,
   the valve body being positioned within the inner bore of the valve housing, and pivotably coupled to the valve housing along the axis of rotation that is positioned between the valve seat and the upper end of the valve housing, the valve body being positioned in a first closed orientation wherein the outer rim corresponds to the seat surface with the seal sealing the first valve side from the second valve side, and a second open orientation wherein the outer rim is pivoted away from the seat surface providing fluid communication between the first valve side and the second valve side, wherein, in the first closed orientation, the valve body is structurally configured to be translatable toward the lower end, thereby directing the outer rim toward the seat surface; and
   further comprising a handle having a lever arm on the outside of the valve housing and a shaft extending through the housing, the shaft defining an axle member at a second end thereof, the valve housing having a valve axle slot opposite the axle member, the valve body further including:
      a first axle protrusion extending from the valve body and into the valve axle slot, the first axle protrusion rotatable within the valve axle slot and translatable when the valve body is in the first closed orientation toward and away from the lower end; and
      a second axle slot, with the axle member of the handle member extending into the second axle slot, the second axle slot configured to cooperate with the axle member to allow rotation of the valve body upon rotation of the handle, and to allow translation of the valve body toward and away from the lower end when in the first closed orientation relative to the axle member,
   wherein, in the first closed orientation the seal biases the second axle slot against the axle member of the lever arm, and the seal biases the first axle protrusion against the valve axle slot.

2. The valve assembly of claim 1 wherein the seal provides a biasing means sufficient to translate the valve body in the first closed orientation toward the upper end.

3. The valve assembly of claim 1 wherein the at least two spaced apart outwardly directed annular flanges further comprises three spaced apart outwardly directed annular flanges, defining a first channel and a second channel therebetween, and a seal positioned within each of the first channel and the second channel.

4. The valve assembly of claim 3 wherein the first channel has a first slope and the second channel has a second slope, wherein the first slope and the second slope are different.

5. The valve assembly of claim 4 wherein the three spaced apart outwardly directed annular flanges are substantially parallel to each other.

6. The valve assembly of claim 1 wherein the axle member and the valve axle slot define the axis of rotation of the valve body relative to the valve housing.

7. The valve assembly of claim 1 wherein the axle member and the valve axle slot are positioned on the second side of the valve.

8. A valve assembly comprising:

a valve housing having a lower end and an upper end, and defining an inner bore, the valve housing including a valve seat spaced apart from the lower end and the upper end, separating the valve housing into a first valve side and a second valve side, the valve seat defining a seat surface that is inclined inwardly and toward the lower end of the valve housing;

a valve body including an outer rim with an outer surface and a central web spanning therebetween, the outer rim including at least two spaced apart outwardly directed annular flanges defining at least one channel therebetween, and a seal positioned within the at least one channel, the outer rim inclined outwardly so as to correspond to the seat surface, with the valve body further having an axis of rotation that extends transversely through the valve body spaced apart from the annular flanges, the valve body being positioned within the inner bore of the valve housing, and pivotably coupled to the valve housing along the axis of rotation that is positioned between the valve seat and the upper end of the valve housing, the valve body being positioned in a first closed orientation wherein the outer rim corresponds to the seat surface with the seal sealing the first valve side from the second valve side, and a second open orientation wherein the outer rim is pivoted away from the seat surface providing fluid communication between the first valve side and the second valve side, wherein, in the first closed orientation, the valve body is structurally configured to be translatable toward the lower end, thereby directing the outer rim toward the seat surface;

wherein the valve housing further includes a base channel at the lower end, the base channel having an inner surface and an outer surface, with a plurality of interlocking teeth positioned on the outer surface, the valve assembly further including:

a valve base having a base flange attachable to a flexible bag, and a upstand portion extending upwardly therefrom defining an inner surface and an outer surface, the inner surface having a plurality of seal beads extending therearound, and the outer surface having a plurality of teeth positioned thereon, the upstand portion insertable into the base receiving channel of the valve housing whereupon insertion, the plurality of seal beads sealingly engaging the inner surface of the base channel, and the interlocking teeth of the base channel interlocking with the teeth of the outer surface of the upstand portion, to in turn, couple the valve base to the valve housing.

9. The valve assembly of claim 8 wherein the central web includes an inner surface facing the first valve side and an outer surface facing the second valve side, the outer surface including a central peak and an annular valley surrounding the central peak, with the outer rim extending beyond the annular valley toward the upper end.

10. The valve assembly of claim 9 wherein the outer rim includes an upper end, wherein the upper end of the rim defines a height that corresponds to the central peak.

11. The valve assembly of claim 10 wherein the central web has a substantially uniform thickness between the annular valley and the central peak.

12. A valve assembly comprising:

a valve housing, the valve housing having a lower end and an upper end, with a valve seat positioned therebetween, the valve seat being inclined inwardly toward the lower end;

a valve body pivotably positionable within the valve housing, and pivoting between a first closed orientation and a second open orientation, the valve body pivotable about an axis that extends through the valve housing positioned between the upper end and the valve seat, wherein, in the first closed orientation, the valve body is configured to translate toward and away from the lower end of the valve housing, the valve body further including an outer rim, the outer rim having at least channel extending about an outer surface thereof, with a seal positioned within the at least one channel, the outer rim having an inner surface opposite the outer surface, and a lower end and an upper end, with the central channel positioned between the lower end and the upper end, the valve body having a central web coupled to the outer rim proximate the lower end thereof with the axis being opposite the at least one channel from the lower end, so that, together with the central web, the outer rim defines a concave structure, such that in the first closed orientation, pressure from the upper end will direct the outer rim radially outwardly by applying pressure on an inner side of the outer rim directly opposite the at least one channel.

13. The valve assembly of claim 12 wherein the central web further includes a central peak extending toward the upper end and an annular valley extending therearound between the central peak and the outer rim.

14. The valve assembly of claim 12 wherein the valve body further includes a plurality of spaced apart seals along the outer surface of the outer rim, each of the spaced apart seals engaging the valve seat in the first closed orientation.

* * * * *